US012559543B2

(12) United States Patent
Willumsen et al.

(10) Patent No.: US 12,559,543 B2
(45) Date of Patent: Feb. 24, 2026

(54) NEO-EPITOPE SPECIFIC ASSAY MEASURING PROTEASE MEDIATED DEGRADATION OF TYPE IV COLLAGEN

(71) Applicant: Nordic Bioscience A/S, Herlev (DK)

(72) Inventors: Nicholas Willumsen, Dyssegard (DK); Christine Jensen, Kobenhavn N (DK); Morten A. Karsdal, Kobenhavn Ø (DK)

(73) Assignee: Nordic Bioscience A/S, Herlev (DK)

( * ) Notice: Subject to any disclaimer, the term of this patent is extended or adjusted under 35 U.S.C. 154(b) by 872 days.

(21) Appl. No.: 17/782,468

(22) PCT Filed: Dec. 3, 2020

(86) PCT No.: PCT/EP2020/084432
§ 371 (c)(1),
(2) Date: Jun. 3, 2022

(87) PCT Pub. No.: WO2021/110818
PCT Pub. Date: Jun. 10, 2021

(65) Prior Publication Data
US 2023/0030529 A1     Feb. 2, 2023

(30) Foreign Application Priority Data
Dec. 5, 2019    (GB) ..................................... 1917819

(51) Int. Cl.
*C07K 16/00*     (2006.01)
*G01N 33/534*     (2006.01)
*G01N 33/574*     (2006.01)

(52) U.S. Cl.
CPC ........... *C07K 16/00* (2013.01); *G01N 33/534* (2013.01); *G01N 33/57488* (2013.01); *G01N 2800/7028* (2013.01)

(58) Field of Classification Search
CPC .... C07K 16/00; C07K 2317/34; C07K 16/18; G01N 33/534; G01N 33/57488; G01N 2800/7028; G01N 33/5743
See application file for complete search history.

(56) References Cited

U.S. PATENT DOCUMENTS 9,606,130 B2     3/2017    Veidal et al.

OTHER PUBLICATIONS

Trujillo et al., T cell-inflamed versus Non-T cell-inflamed tumors: a conceptual framework for cancer immunotherapy drug development and combination therapy selection. Cancer Immunology Res., 6(9):990-1000, Sep. 2018.

Salmon et al., Matrix architecture defines the preferential localization and migration of T cells into the stroma of human lung tumors. Journal of Clinical Investigation. 2012;122(3):899-910, 2012.
Nissen et al., Collagens and Cancer associated fibroblasts in the reactive stroma and its relation to Cancer biology. Journal of Experimental and Clinical Cancer Research, 38:115-2019.
Chakravarthy et al., TGF-β-associated extracellular matrix genes link cancer-associated fibroblasts to immune evasion and immunotherapy failure. Nature Communications, 9:4692, 2018.
Mariathasen et al., TGFβ attenuates tumour response to PD-L1 blockade by contributing to exclusion of T cells. Nature, 554(7693):544-548, Feb. 22, 2018.
Jensen et al., Non-invasive biomarkers derived from the extracellular matrix associate with response to immune checkpoint blockade (anti-CTLA-4) in metastatic melanoma patients. Journal for ImmunoTherapy of Cancer, 6:152, 2018.
Kehlet et al., Excessive collagen turnover products are released during colorectal cancer progression and elevated in serum from metastatic colorectal cancer patients. Scientific Reports, 6(1):30599, 2016.
Bager et al., Collagen degradation products measured in serum can separate ovarian and breast cancer patients from healthy controls: A preliminary study. Cancer Biomarkers, 15(6):783-788, 2015.
Prakash et al., Granzyme B promotes cytotoxic lymphocyte transmigration via basement membrane remodeling. Immunity, 41:160-172, Dec. 18, 2014.
St-Pierre et al., T cell control of extracellular matrix degradation. Developmental Immunology. 7(2-4):171-177, 2000.
El-Shabrawi et al., Inhibition of MMP-dependent chemotaxis and amelioration of experimental autoimmune uveitis with a selective metalloproteinase-2 and -9 inhibitor, Journal of Neuroimmunology, 155(1):13-20, 2004.
Leppert et al., Stimulation of matrix metalloproteinase-dependent migration of T cells by eicosanoids. FASEB Journal, 9(14):1473-1481, 1995.
Edsparr et al., Matrix metalloproteinases in cytotoxic lymphocytes impact on tumour infiltration and immunomodulation. Cancer Microenvironment, 4:351-360, 2011.
Combet et al., NPS@: network protein sequence analysis. Trends in biochemical sciences, 25(3):147-150, Mar. 2000.
Gefter et al., A simple method for polyethylene glycol-promoted hybridization of mouse myeloma cells. Somatic Cell Genetics, 3(2):231-236, 1977.
Sand et al., MMP mediated degradation of type IV collagen alpha 1 and alpha 3 chains reflects basement membrane remodeling in experimental and clinical fibrosis—Validation of two novel biomarker assays. PLoS One. 8(12):e84934 , Dec. 23, 2013.
Kabat et al., Sequences of Proteins of Immunological Interest, United States Department of Health and Human Services, Bethesda, Md., p. 1, 1987.

*Primary Examiner* — Kimberly Ballard
*Assistant Examiner* — Stacey N MacFarlane
(74) *Attorney, Agent, or Firm* — Benjamin Aaron Adler

(57) ABSTRACT

An assay measuring protease mediated degradation of type IV collagen and its biomarker potential for identifying cancer patients with a T-cell permissive tumor microenvironment is described.

19 Claims, 5 Drawing Sheets
Specification includes a Sequence Listing.

SEQUENCE LISTING

```
<160> NUMBER OF SEQ ID NOS: 21

<210> SEQ ID NO 1
<211> LENGTH: 10
<212> TYPE: PRT
<213> ORGANISM: Artificial sequence
<220> FEATURE:
<223> OTHER INFORMATION: N-terminus epitope sequence C4G from collagen
      Type IV ?2 chain

<400> SEQUENCE: 1

Met Gly Asn Thr Gly Pro Thr Gly Ala Val
1               5                   10

<210> SEQ ID NO 2
<211> LENGTH: 11
<212> TYPE: PRT
<213> ORGANISM: Artificial sequence
<220> FEATURE:
<223> OTHER INFORMATION: Elongated C4G sequence
<220> FEATURE:
<221> NAME/KEY: SITE
<222> LOCATION: 1
<223> OTHER INFORMATION: Xaa is any amino acid

<400> SEQUENCE: 2

Xaa Met Gly Asn Thr Gly Pro Thr Gly Ala Val
1               5                   10

<210> SEQ ID NO 3
<211> LENGTH: 9
<212> TYPE: PRT
<213> ORGANISM: Artificial sequence
<220> FEATURE:
<223> OTHER INFORMATION: Truncated C4G sequence

<400> SEQUENCE: 3

Gly Asn Thr Gly Pro Thr Gly Ala Val
1               5

<210> SEQ ID NO 4
<211> LENGTH: 10
<212> TYPE: PRT
<213> ORGANISM: Artificial sequence
<220> FEATURE:
<223> OTHER INFORMATION: Mutated C4G sequence

<400> SEQUENCE: 4

Met Gly Gln Thr Gly Pro Thr Gly Ala Val
1               5                   10
```

<210> SEQ ID NO 5
<211> LENGTH: 10
<212> TYPE: PRT
<213> ORGANISM: Artificial sequence
<220> FEATURE:
<223> OTHER INFORMATION: Mutated C4G sequence

<400> SEQUENCE: 5

Met Gly Asn Ser Gly Pro Thr Gly Ala Val
1               5                   10

<210> SEQ ID NO 6
<211> LENGTH: 10
<212> TYPE: PRT
<213> ORGANISM: Artificial sequence
<220> FEATURE:
<223> OTHER INFORMATION: Mutated C4G sequence

<400> SEQUENCE: 6

Gln Gly Asn Thr Gly Pro Thr Gly Ala Val
1               5                   10

<210> SEQ ID NO 7
<211> LENGTH: 11
<212> TYPE: PRT
<213> ORGANISM: Artificial sequence
<220> FEATURE:
<223> OTHER INFORMATION: Mutated C4G sequence

<400> SEQUENCE: 7

Phe Met Gly Asn Thr Gly Pro Thr Gly Ala Val
1               5                   10

<210> SEQ ID NO 8
<211> LENGTH: 16
<212> TYPE: PRT
<213> ORGANISM: Artificial sequence
<220> FEATURE:
<223> OTHER INFORMATION: C4G antibody light chain complementarity-
      determining region CDR-L1

<400> SEQUENCE: 8

Lys Ser Ser Gln Ser Leu Leu Tyr Ser Asp Gly Lys Thr Tyr Leu Asn
1               5                   10                  15

<210> SEQ ID NO 9
<211> LENGTH: 7
<212> TYPE: PRT
<213> ORGANISM: Artificial sequence
<220> FEATURE:
<223> OTHER INFORMATION: C4G antibody light chain complementarity-
      determining region CDR-L2

<400> SEQUENCE: 9

Leu Val Ser Lys Leu Asp Ser
1               5

<210> SEQ ID NO 10
<211> LENGTH: 8
<212> TYPE: PRT
<213> ORGANISM: Artificial sequence
<220> FEATURE:
<223> OTHER INFORMATION: C4G antibody light chain complementarity-
      determining region CDR-L3

<400> SEQUENCE: 10

```
Trp Gln Gly Thr His Phe Val Thr
1               5

<210> SEQ ID NO 11
<211> LENGTH: 7
<212> TYPE: PRT
<213> ORGANISM: Artificial sequence
<220> FEATURE:
<223> OTHER INFORMATION: C4G antibody heavy chain complementarity-
      determining region CDR-H1

<400> SEQUENCE: 11

Thr Tyr Asn Ile Gly Val Gly
1               5

<210> SEQ ID NO 12
<211> LENGTH: 16
<212> TYPE: PRT
<213> ORGANISM: Artificial sequence
<220> FEATURE:
<223> OTHER INFORMATION: C4G antibody heavy chain complementarity-
      determining region CDR-H2

<400> SEQUENCE: 12

His Ile Trp Tyr Asn Asp Ile Lys Tyr Tyr Asn Thr Ala Leu Lys Ser
1               5                   10                  15

<210> SEQ ID NO 13
<211> LENGTH: 8
<212> TYPE: PRT
<213> ORGANISM: Artificial sequence
<220> FEATURE:
<223> OTHER INFORMATION: C4G antibody heavy chain complementarity-
      determining region CDR-H3

<400> SEQUENCE: 13

Leu Arg Pro Asp Ser Phe Asp Tyr
1               5

<210> SEQ ID NO 14
<211> LENGTH: 78
<212> TYPE: PRT
<213> ORGANISM: Artificial sequence
<220> FEATURE:
<223> OTHER INFORMATION: C4G antibody light chain with complementarity-
      determining regions and framework sequences

<400> SEQUENCE: 14

Lys Ser Ser Gln Ser Leu Leu Tyr Ser Asp Gly Lys Thr Tyr Leu Asn
1               5                   10                  15

Trp Leu Leu Leu Arg Pro Gly Gln Ser Pro Lys Arg Leu Ile Tyr Leu
            20                  25                  30

Val Ser Lys Leu Asp Ser Gly Val Pro Asp Arg Phe Thr Gly Ser Gly
        35                  40                  45

Ser Gly Thr Asp Phe Thr Leu Lys Ile Ser Arg Val Glu Ala Glu Asp
    50                  55                  60

Leu Gly Val Tyr Tyr Cys Trp Gln Gly Thr His Phe Val Thr
65                  70                  75

<210> SEQ ID NO 15
<211> LENGTH: 77
<212> TYPE: PRT
<213> ORGANISM: Artificial sequence
<220> FEATURE:
<223> OTHER INFORMATION: C4G antibody heavy chain with complementarity-
      determining regions and framework sequences
```

-continued

<400> SEQUENCE: 15

```
Thr Tyr Asn Ile Gly Val Gly Trp Ile Arg Gln Ser Ser Gly Lys Gly
1               5                   10                  15

Leu Glu Trp Leu Ala His Ile Trp Tyr Asn Asp Ile Lys Tyr Tyr Asn
            20                  25                  30

Thr Ala Leu Lys Ser Arg Leu Thr Ile Ser Lys Asp Thr Ser Asn Asn
        35                  40                  45

Gln Val Phe Leu Lys Ile Ala Ser Val Val Thr Ala Asp Thr Ala Thr
    50                  55                  60

Tyr Tyr Cys Ala Arg Leu Arg Pro Asp Ser Phe Asp Tyr
65                  70                  75
```

<210> SEQ ID NO 16
<211> LENGTH: 111
<212> TYPE: PRT
<213> ORGANISM: Artificial sequence
<220> FEATURE:
<223> OTHER INFORMATION: C4G antibody light chain variable region
      sequence

<400> SEQUENCE: 16

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Leu Leu Leu Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Val Thr Phe Gly Ala Gly Thr Lys Leu Glu Leu Lys
                100                 105                 110
```

<210> SEQ ID NO 17
<211> LENGTH: 118
<212> TYPE: PRT
<213> ORGANISM: Artificial sequence
<220> FEATURE:
<223> OTHER INFORMATION: C4G antibody heavy chain variable region
      sequence

<400> SEQUENCE: 17

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
            20                  25                  30

Asn Ile Gly Val Gly Trp Ile Arg Gln Ser Ser Gly Lys Gly Leu Glu
        35                  40                  45

Trp Leu Ala His Ile Trp Tyr Asn Asp Ile Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Val Thr Ala Asp Thr Ala Thr Tyr Tyr
                85                  90                  95
```

Cys Ala Arg Leu Arg Pro Asp Ser Phe Asp Tyr Trp Gly Gln Gly Thr
            100                 105                 110

Thr Leu Thr Val Ser Ser
        115

<210> SEQ ID NO 18
<211> LENGTH: 10
<212> TYPE: PRT
<213> ORGANISM: Artificial Sequence
<220> FEATURE:
<223> OTHER INFORMATION: Nonsense peptide

<400> SEQUENCE: 18

Leu Leu Ala Arg Asp Phe Glu Lys Asn Tyr
1               5                   10

<210> SEQ ID NO 19
<211> LENGTH: 11
<212> TYPE: PRT
<213> ORGANISM: Artificial Sequence
<220> FEATURE:
<221> NAME/KEY: SITE
<222> LOCATION: 11
<223> OTHER INFORMATION: Linker residue
<220> FEATURE:
<221> NAME/KEY: SITE
<222> LOCATION: 11
<223> OTHER INFORMATION: Biotin

<400> SEQUENCE: 19

Leu Leu Ala Arg Asp Phe Glu Lys Asn Tyr Lys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Immunogenic peptide
<220> FEATURE:
<221> NAME/KEY: SITE
<222> LOCATION: 11..13
<223> OTHER INFORMATION: Linker peptide
<220> FEATURE:
<221> NAME/KEY: SITE
<222> LOCATION: 13
<223> OTHER INFORMATION: Keyhole limpet hemocyanin

<400> SEQUENCE: 20

Met Gly Asn Thr Gly Pro Thr Gly Ala Val Gly Gly Cys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Biotinylated coating peptide
<220> FEATURE:
<221> NAME/KEY: SITE
<222> LOCATION: 10
<223> OTHER INFORMATION: Linker residue
<220> FEATURE:
<221> NAME/KEY: SITE
<222> LOCATION: 13
<223> OTHER INFORMATION: Biotin

<400> SEQUENCE: 21

```
Met Gly Asn Thr Gly Pro Thr Ala Val Lys
1               5                   10
```

NEO-EPITOPE SPECIFIC ASSAY MEASURING PROTEASE MEDIATED DEGRADATION OF TYPE IV COLLAGEN

FIELD OF THE INVENTION

The present invention relates to an assay measuring protease mediated degradation of type IV collagen and its biomarker potential for identifying cancer patients with a T-cell permissive tumor microenvironment.

INTRODUCTION

Immunotherapy with immune checkpoint inhibitors have revolutionized cancer treatment by giving an opportunity of durable response (1). Immune checkpoint inhibitor treatment involves antibodies, as anti-CTLA-4, anti-PD1 and anti-PD-L1, that reactivate cytotoxic T lymphocytes so they can eliminate tumor cells. But despite clinical success of these immune checkpoint inhibitors, only a subset of cancer patients has a long-term survival benefit. Thus, it is important to identify non-invasive biomarkers that can identify the cancer patients that will respond to immune checkpoint inhibitor therapy to avoid wrong treatment and adverse events. For identifying predictive biomarkers, it is vital to understand some of factors that influence response and resistance.

Three different immune profiles of patients before receiving therapy have been identified that correlate with a person's response to immune checkpoint therapy (2). Clinical responses occur most often in patients with an immune-inflamed tumor type, which is characterized by the presence of CD4- and CD8 expressing T cells in the tumor microenvironment near the tumor cells. The immune-excluded phenotype is characterized by the presence of immune cells, but they are retained in the surrounding stroma, which block T-cell infiltration. In the immune-desert phenotype, there is no T cells in either the tumor parenchyma or stroma.

Patients with an immune-excluded or immune-desert phenotype rarely respond to immune checkpoint inhibitor therapy, so biomarkers identifying an immune-inflamed tumor type could be a very useful predictive tool. For efficient cancer immunotherapy is it important that the T cells are both activated and recruited to the tumor microenvironment defining an immune-inflamed phenotype ("hot tumor") (3).

The composition of the extracellular matrix (ECM) has been shown to affect the location and migration of T cells and identified to have a crucial role in resistance to immunotherapy (4-7). We have previously shown that the serological biomarker PRO-C3 reflecting excessive type Ill collagen formation (desmoplasia) and the biomarker C4M reflecting matrix metalloproteinase (MMP)-9 degraded type IV collagen are associated to poor response to immune checkpoint blockade (8). In addition to this, C4M is elevated in different cancer patients (9,10).

Interestingly, T cells also express proteases that induce an invasive behavior in the T cells (11,12). It has been shown that transmigrating T cells secrete MMPs and serine proteases (Granzyme B) to pass through basement membranes on route into the underlying tissue (11,13-15).

SUMMARY OF THE INVENTION

Type IV collagen is the main component of the basement membrane, hence the present inventors hypothesized that specific protease generated type IV collagen fragments are released into the circulation of cancer patients as part of T-cell transmigration from the circulation into the tumor microenvironment. These type IV collagen fragments could therefore have biomarker potential of identifying cancer patients with a T-cell permissive tumor microenvironment that respond to immune checkpoint inhibitor treatment. The present inventors have now developed a competitive electro-chemiluminescence immunoassay (ECLIA) targeting a neo-epitope of protease mediated degradation of type IV collagen and have shown that its levels are elevated in serum from metastatic melanoma patients successfully treated with the immune checkpoint inhibitor Ipilimumab. To further evaluate the potential, this biomarker was also assessed in serum from patients with different kinds of cancer. The biomarker can also be used to provide a prognosis for survival in patients with cancer, in particular pancreas ductal adenocarcinoma.

Accordingly, in a first aspect the present invention relates to a monoclonal antibody that specifically recognises and binds to a peptide having the N-terminus amino acid sequence MGNTGPTGAV (SEQ ID No. 1) (also referred to herein as the target peptide or C4aa[1355]). This peptide sequence represents a neo-epitope generated by digestion of collagen Type IV α2 chain with a protease, such as a serine protease (e.g. Granzyme B) or a matrix metalloproteinase (e.g. MMP-9), which causes cleavage between amino acids F[1354] and M[1355].

Preferably said monoclonal antibody does not recognize or specifically bind to an elongated version of said N-terminus amino acid sequence, which is XMGNTGPTGAV (SEQ ID No. 2), wherein X is any amino acid. Preferably X is F. Preferably said monoclonal antibody does not recognize or specifically bind to a truncated version of said N-terminus amino acid sequence, in particular the peptide which is GNTGPTGAV (SEQ ID No. 3). Preferably said monoclonal antibody does not recognize or specifically bind to a mutated version of said N-terminus amino acid sequence which is MGQTGPTGAV (SEQ ID No. 4), MGNSGPTGAV (SEQ ID No. 5) and/or QGNTGPTGAV (SEQ ID No. 6).

Preferably, the ratio of the affinity of said antibody for the N-terminus amino acid sequence MGNTGPTGAV (SEQ ID No. 1) to the affinity of said antibody for the elongated N-terminus amino acid sequence FMGNTGPTGAV (SEQ ID No. 7) is at least 10 to 1, and more preferably is at least 50 to 1, at least 100 to 1, at least 500 to 1, at least 1,000 to 1, at least 10,000 to 1, at least 100,000 to 1, or at least 1,000,000 to 1.

Preferably, the ratio of the affinity of said antibody for the N-terminus amino acid sequence MGNTGPTGAV (SEQ ID No. 1) to the affinity of said antibody for the truncated N-terminus amino acid sequence GNTGPTGAV (SEQ ID No. 3) is at least 10 to 1, and more preferably is at least 50 to 1, at least 100 to 1, at least 500 to 1, at least 1,000 to 1, at least 10,000 to 1, at least 100,000 to 1, or at least 1,000,000 to 1.

Preferably, the ratio of the affinity of said antibody for the N-terminus amino acid sequence MGNTGPTGAV (SEQ ID No. 1) to the affinity of said antibody for the mutated N-terminus amino acid sequence MGQTGPTGAV (SEQ ID No. 4) is at least 10 to 1, and more preferably is at least 50 to 1, at least 100 to 1, at least 500 to 1, at least 1,000 to 1, at least 10,000 to 1, at least 100,000 to 1, or at least 1,000,000 to 1.

Preferably, the ratio of the affinity of said antibody for the N-terminus amino acid sequence MGNTGPTGAV (SEQ ID No. 1) to the affinity of said antibody for the mutated N-terminus amino acid sequence MGNSGPTGAV (SEQ ID No. 5) is at least 10 to 1, and more preferably is at least 50 to 1, at least 100 to 1, at least 500 to 1, at least 1,000 to 1, at least 10,000 to 1, at least 100,000 to 1, or at least 1,000,000 to 1.

Preferably, the ratio of the affinity of said antibody for the N-terminus amino acid sequence MGNTGPTGAV (SEQ ID No. 1) to the affinity of said antibody for the mutated N-terminus amino acid sequence QGNTGPTGAV (SEQ ID No. 6) is at least 10 to 1, and more preferably is at least 50 to 1, at least 100 to 1, at least 500 to 1, at least 1,000 to 1, at least 10,000 to 1, at least 100,000 to 1, or at least 1,000,000 to 1.

Monoclonal antibodies that specifically bind to the N-terminus amino acid sequence MGNTGPTGAV (SEQ ID No. 1) can be generated via any suitable techniques known in the art. For example, the monoclonal antibody may be raised against a synthetic peptide having the amino acid sequence MGNTGPTGAV (SEQ ID No. 1), such as for example by: immunizing a rodent (or other suitable mammal) with a synthetic peptide consisting of the sequence MGNTGPTGAV (SEQ ID No. 1), which optionally may linked to an immunogenic carrier protein (such as keyhole limpet hemocyanin), isolating and cloning a single antibody producing cell, and assaying the resulting monoclonal antibodies to ensure that they have the desired specificity. An exemplary protocol for producing a monoclonal antibody that that specifically bind to the N-terminus amino acid sequence MGNTGPTGAV (SEQ ID No. 1) is described infra.

Preferably, the monoclonal antibody or fragment thereof may preferably comprise one or more complementarity-determining regions (CDRs) selected from:

```
CDR-L1:
                                (SEQ ID No. 8)
KSSQSLLYSDGKTYLN

CDR-L2:
                                (SEQ ID No. 9)
LVSKLDS

CDR-L3:
                                (SEQ ID No. 10)
WQGTHFVT

CDR-H1:
                                (SEQ ID No. 11)
TYNIGVG

CDR-H2:
                                (SEQ ID No. 12)
HIWYNDIKYYNTALKS
and

CDR-H3:
                                (SEQ ID No. 13)
LRPDSFDY.
```

Preferably the antibody or fragment thereof comprises at least 2, 3, 4, 5 or 6 of the above listed CDR sequences.

Preferably the monoclonal antibody or fragment thereof has a light chain variable region comprising the CDR sequences

```
CDR-L1:
                                (SEQ ID No. 8)
KSSQSLLYSDGKTYLN

CDR-L2:
                                (SEQ ID No. 9)
LVSKLDS
```

```
             -continued
and

CDR-L3:
                                (SEQ ID No. 10)
WQGTHFVT.
```

Preferably the monoclonal antibody or fragment thereof has a light chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics).

```
                                (SEQ ID No. 14)
KSSQSLLYSDGKTYLNWLLLRPGQSPKRLIYLVSKLDSGVPDRFTGSGS
GTDFTLKISRVEAEDLGVYYCWQGTHFVT
```

Preferably the monoclonal antibody or fragment thereof has a heavy chain variable region comprising the CDR sequences

```
CDR-H1:
                                (SEQ ID No. 11)
TYNIGVG

CDR-H2:
                                (SEQ ID No. 12)
HIWYNDIKYYNTALKS
and

CDR-H3:
                                (SEQ ID No. 13)
LRPDSFDY.
```

Preferably the monoclonal antibody or fragment thereof has a heavy chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics).

```
                                (SEQ ID No. 15)
TYNIGVGWIRQSSGKGLEWLAHIWYNDIKYYNTALKSRLTISKDTSNNQ
VFLKIASVVTADTATYYCARLRPDSFDY
```

As used herein, the framework amino acid sequences between the CDRs of an antibody are substantially identical or substantially similar to the framework amino acid sequences between the CDRs of another antibody if they have at least 70%, 80%, 90% or at least 95% similarity or identity. The similar or identical amino acids may be contiguous or non-contiguous.

The framework sequences may contain one or more amino acid substitutions, insertions and/or deletions. Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1 Ala, Ser, Thr, Pro, Gly; Group 2 Asp, Asn, Glu, Gln; Group 3 His, Arg, Lys; Group 4 Met, Leu, Ile, Val, Cys; Group 5 Phe Thy Trp.

A program such as the CLUSTAL program to can be used to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention. Identity or similarity is preferably calculated over the entire length of the framework sequences.

In certain preferred embodiments, the monoclonal antibody or fragment thereof may comprise the light chain variable region sequence:

(SEQ ID No. 16)
*DVVMTQTPLTLSVTIGQPASISC*KSSQSLLYSDGKTYLN*WLLLRPGQSP*
*KRLIY*LVSKLDS*GVPDRFTGSGSGTDFTLKISRVEAEDLGVYYC***WQGTH*
FVT*FGAGTKLELK*
(CDRs bold and underlined; Framework sequences in italics)

and/or the heavy chain variable region sequence:

(SEQ ID No. 17)
*QVTLKESGPGILQPSQTLSLTCSFSGFSLT*TYNIGVG*WIRQSSGKGLE*
*WLA*HIWYNDIKYYNTALKS*RLTISKDTSNNQVFLKIASVVTADTATYY*
*CAR*LRPDSFDY*WGQGTTLTVSS*
(CDRs bold and underlined; Framework sequences in italics).

In a second aspect, the present invention relates to a method for identifying if a subject with cancer will respond to immunotherapy, said method comprising detecting the presence of a peptide having the N-terminus amino acid sequence MGNTGPTGAV (SEQ ID No. 1) in a sample obtained from the subject. The sample is preferably a biofluid sample, in particular a human biofluid sample.

Preferably, the immunotherapy comprises at least one immune checkpoint inhibitor. Immune check point inhibitors target molecules on some immune cells that need to be activated (or inactivated) in order to initiate an immune response. These checkpoint proteins include PD-1, PD-L1, and CTLA-4. Immune checkpoint inhibitors can target any one or more of these molecules. Immune checkpoint inhibitors include ipilimumab, pembrolizumab, nivolumab, atezolizumab, avelumab, durvalumab, cemiplimab or combinations thereof. Preferably, the immune check point inhibitor may target CTLA-4, such as Ipilimumab. Alternatively, the immune check point inhibitor may target PD-1, for example pembrolizumab, nivolumab and/or cemiplimab. Alternatively, the immune checkpoint inhibitor may target PD-L1, for example atezolizumab, avelumab, or durvalumab. Preferably, the immunotherapy with at least one immune checkpoint inhibitor comprises administering Ipilimumab.

Preferably the method is an immunoassay. More preferably the method comprises contacting a biofluid sample obtained from the subject with a monoclonal antibody according to the first aspect of the invention, and detecting binding between the monoclonal antibody and peptides in the sample.

The method according to the second aspect utilizes a monoclonal antibody of the first aspect, and accordingly preferred embodiments of the second aspect will be apparent from the above discussion of the preferred embodiments of the first aspect.

Preferably, the detection is quantitative. Thus, the method may comprise detecting and determining the amount of binding between the monoclonal antibody and peptides in the sample.

Preferably, the immunoassay is a competitive immunoassay.

Preferably, the immunoassay is an enzyme-linked immunosorbent assay (ELISA) or electro-chemiluminescence immunoassay (ECLIA). Preferably the ELISA is a competitive ELISA.

Preferably the ECLIA is a competitive ECLIA.

The biofluid sample may be, but is not limited to, blood, serum, plasma, urine or a supernatant from cell or tissue cultures. Preferably the biofluid is serum or plasma, most preferably serum.

In the method of the second aspect, the sample is obtained from a subject who has been diagnosed with a cancer. The cancer may be metastatic. The cancer is preferably selected from melanoma, breast, colorectal, gastric, non-small cell lung cancer, small cell lung cancer, ovarian, prostate or pancreatic cancer, including pancreas ductal adenocarcinoma. Preferably the subject has melanoma, in particular a metastatic melanoma.

The method may further comprise correlating the amount of peptide detected with values associated with normal healthy subjects and/or values obtained from cancer patients who have clinically responded to immunotherapy, for example patients who have prolonged survival time, tumor shrinkage and/or improvement in symptoms following treatment. Elevated levels of the peptide may be indicative that the subject has an immune-inflamed tumor type, and so would be responsive to immunotherapy.

As used herein the term "values associated with normal healthy subjects and/or values obtained from cancer patients who have responded to immunotherapy" means standardised quantities determined by the method described supra for subjects considered to be healthy, i.e. without a cancer, and/or standardised quantities determined by the method described supra for subjects known to have a cancer who have responded clinically to treatment with immunotherapy, preferably an immune checkpoint inhibitor, for example reduction in tumor size, improvements in symptoms and/or longer overall survival time.

In some embodiments of the method according to the second aspect, the amount of binding of the monoclonal antibody specific for the epitope of type IV collagen peptide with N-terminal amino acid sequence MGNTGPTGAV (SEQ ID No. 1) is correlated with one or more predetermined cut-off values.

As used herein the "cut-off value" means an amount of binding that is determined statistically to be indicative of a high likelihood of responding to immunotherapy with an immune checkpoint inhibitor. The measured value of biomarker binding in a patient sample that is at or above the statistical cutoff value may correspond to at least a 70% probability, preferably at least an 80% probability, preferably at least an 85% probability, more preferably at least a 90% probability, and most preferably at least a 95% probability of the presence or likelihood of responding to immunotherapy, preferably with an immune checkpoint inhibitor, indicated by a reduction in tumor size, improvement in symptoms and/or longer overall survival time. The "cut-off value" can be calculated by comparing the results obtained from patients who have been diagnosed with a cancer and have responded to immunotherapy with results obtained from patients who have been diagnosed with the same cancer but have not responded to immunotherapy.

If the measured amount of binding of the monoclonal antibody specific for the N-terminal amino acid sequence MGNTGPTGAV (SEQ ID No. 1) is in the top three quartiles (Q2+Q3+Q4) of levels measured in cancer patients, in particular patients with the same kind of cancer, this indicates that the patient is likely to respond to treatment with an immune checkpoint inhibitor.

The predetermined cut-off value for the amount of binding of the monoclonal antibody specific for the N-terminal amino acid sequence MGNTGPTGAV (SEQ ID No. 1) may be within the range 10.0-20.0 ng/mL. Preferably the predetermined cut-off value for the amount of binding of the monoclonal antibody specific for the N-terminal amino acid sequence MGNTGPTGAV (SEQ ID No. 1) is at least 14.5 ng/mL. In this regard, through the use of statistical analyses it has been found that a measured amount of binding of the monoclonal antibody specific for the N-terminal amino acid sequence MGNTGPTGAV (SEQ ID No. 1) of at least 14.5 ng/mL or greater may be determinative of a patient likely to respond to immunotherapy, preferably with an immune checkpoint inhibitor. By having a statistical cut-off value of at least 14.5 ng/mL it is possible to utilise the method of the invention to give a prediction of response to immunotherapy with a high level of confidence. In particular, at least 14.5 ng/mL or greater may be determinative of a patient with melanoma likely to respond to immunotherapy. Applying such statistical cut-off values are particularly advantageous as it results in a standalone diagnostic assay; i.e. it removes the need for any direct comparisons with healthy individuals and/or patients known to have responded to immunotherapy, preferably those who have responded to treatment with an immune checkpoint inhibitor in order to arrive at a diagnostic conclusion. An expedited conclusive prediction may result in the patients likely to respond being treated at an earlier stage, which may in turn improve overall chances of survival, and/or reduce the risk of hospitalisation.

The method may further comprise administering immunotherapy to the subject determined to have an elevated level of the peptide present.

In a third aspect, the present invention relates to an assay kit comprising a monoclonal antibody that specifically recognises and binds to a peptide having the N-terminus amino acid sequence MGNTGPTGAV (SEQ ID No. 1), and at least one of:

a streptavidin coated well plate;
a C-terminal biotinylated peptide having the N-terminus amino acid sequence MGNTGPTGAV (SEQ ID No. 1);
a calibrator peptide having the N-terminus amino acid sequence MGNTGPTGAV (SEQ ID No. 1),
an antibody biotinylation kit;
an antibody HRP labeling kit;
an antibody radiolabeling kit; and
an assay visualization kit.

The kit may be used in identifying cancer patients who will respond to immunotherapy, preferably treatment with an immune checkpoint inhibitor.

The immunoassay kit is suitable for carrying out a method according to the second aspect and contains a monoclonal antibody according to the first aspect and accordingly preferred embodiments of the third aspect will be apparent from the above discussion of the preferred embodiments of the first aspect and the second aspect.

In a fourth aspect, the present invention also relates to a method of treating a subject who has been diagnosed with a cancer, and who is known to have an elevated level of the peptide C4-aa$^{1355}$ with an immunotherapy. Preferably the immunotherapy comprises at least one immune checkpoint inhibitor. As used herein "elevated level of the peptide C4-aa$^{1355n}$" refers to an amount of the peptide which is significantly higher than the amount detected in a normal healthy control and/or a subject who has been diagnosed with cancer, but who has not responded to immunotherapy, in particular an immune checkpoint inhibitor.

The cancer may be metastatic. The cancer is preferably selected from melanoma, breast, colorectal, gastric, non-small cell lung cancer, small cell lung cancer, ovarian, prostate or pancreatic cancer including pancreas ductal adenocarcinoma. Preferably the subject has melanoma, in particular a metastatic melanoma.

In a fifth aspect, the present invention also relates to a method for predicting survival outcome of a subject with cancer, said method comprising detecting the presence of a peptide having the N-terminus amino acid sequence MGNTGPTGAV (SEQ ID No. 1).

Preferably the method is an immunoassay. More preferably the method comprises contacting a biofluid sample obtained from the subject with a monoclonal antibody according to the first aspect of the invention, and detecting binding between the monoclonal antibody and peptides in the sample.

The method according to the fifth aspect utilizes a monoclonal antibody of the first aspect, and accordingly preferred embodiments of the fifth aspect will be apparent from the above discussion of the preferred embodiments of the first aspect.

Preferably, the detection is quantitative. Thus the method may comprise detecting and determining the amount of binding between the monoclonal antibody and peptides in the sample.

Preferably, the immunoassay is a competitive immunoassay.

Preferably, the immunoassay is an enzyme-linked immunosorbent assay (ELISA) or electro-chemiluminescence immunoassay (ECLIA). Preferably the ELISA is a competitive ELISA. Preferably the ECLIA is a competitive ECLIA.

The biofluid sample may be, but is not limited to, blood, serum, plasma, urine or a supernatant from cell or tissue cultures. Preferably the biofluid is serum or plasma, most preferably serum.

In the method of the second aspect, the sample is obtained from a subject who has been diagnosed with a cancer. The cancer is preferably selected from melanoma, breast, colorectal, gastric, non-small cell lung cancer, small cell lung cancer, ovarian, prostate or pancreatic cancer, including pancreas ductal adenocarcinoma. Preferably the subject has pancreatic cancer, more preferably pancreas ductal adenocarcinoma.

The method may further comprise correlating the amount of peptide detected with values associated with normal healthy subjects and/or values obtained from cancer patients for example patients who have been diagnosed with the same cancer. If the measured amount of binding of the monoclonal antibody specific for the N-terminal amino acid sequence MGNTGPTGAV (SEQ ID No. 1) is in the top or bottom quartiles (Q1 or Q4) of levels measured in cancer patients, in particular patients with the same kind of cancer, this indicates that the patient is likely to have a poor prognosis and increased risk of death. If the measured amount of binding of the monoclonal antibody specific for the N-terminal amino acid sequence MGNTGPTGAV (SEQ ID No. 1) is in the middle quartiles (Q2+Q3) of levels measured in cancer patients, in particular patients with the same kind of cancer, this indicates that the patient has a reduced risk of death.

As used herein the term "values associated with normal healthy subjects and/or values obtained from cancer patients" means standardised quantities determined by the method described supra for subjects considered to be healthy, i.e. without a cancer, and/or standardised quantities determined by the method described supra for subjects known to have a cancer.

In some embodiments of the method according to the fifth aspect, the amount of binding of the monoclonal antibody specific for the epitope of type IV collagen peptide with N-terminal amino acid sequence MGNTGPTGAV (SEQ ID No. 1) is correlated with one or more predetermined cut-off values.

As used herein the "cut-off value" means an amount of binding that is determined statistically to be indicative of a reduced risk of dying. The measured value of biomarker binding in a patient sample that is within the statistical cutoff values may correspond to at least a 70% probability, preferably at least an 80% probability, preferably at least an 85% probability, more preferably at least a 90% probability, and most preferably at least a 95% probability of reduced risk of death. The "cut-off value" can be calculated by comparing the results obtained from patients who have been diagnosed with a cancer and have a known survival time.

Definitions

As used herein, the terms "peptide" and "polypeptide" are used synonymously.

As used herein the term "monoclonal antibody" refers to both whole antibodies and to fragments thereof that retain the binding specificity of the whole antibody, such as for example a Fab fragment, F(ab')2 fragment, single chain Fv fragment, or other such fragments known to those skilled in the art. As is well known, whole antibodies typically have a "Y-shaped" structure of two identical pairs of polypeptide chains, each pair made up of one "light" and one "heavy" chain. The N-terminal regions of each light chain and heavy chain contain the variable region, while the C-terminal portions of each of the heavy and light chains make up the constant region. The variable region comprises three complementarity determining regions (CDRs), which are primarily responsible for antigen recognition. The constant region allows the antibody to recruit cells and molecules of the immune system. Antibody fragments retaining binding specificity comprise at least the CDRs and sufficient parts of the rest of the variable region to retain said binding specificity.

In the present invention, the monoclonal antibody may comprise any constant region known in the art. Human constant light chains are classified as kappa and lambda light chains. Heavy constant chains are classified as mu, delta, gamma, alpha, or epsilon, and define the antibody's isotype as IgM, IgD, IgG, IgA, and IgE, respectively. The IgG isotype has several subclasses, including, but not limited to IgG1, IgG2, IgG3, and IgG4. The monoclonal antibody may preferably be of the IgG isotype, including any one of IgG1, IgG2, IgG3 or IgG4.

The CDR of an antibody can be determined using methods known in the art such as that described by Kabat et al[19]. Antibodies can be generated from B cell clones as described in the examples. The isotype of the antibody can be determined by ELISA specific for human IgM, IgG or IgA isotype, or human IgG1, IgG2, IgG3 or IgG4 subclasses. The amino acid sequence of the antibodies generated can be determined using standard techniques. For example, RNA can be isolated from the cells, and used to generate cDNA by reverse transcription. The cDNA is then subjected to PCR using primers which amplify the heavy and light chains of the antibody. For example primers specific for the leader sequence for all VH (variable heavy chain) sequences can be used together with primers that bind to a sequence located in the constant region of the isotype which has been previously determined. The light chain can be amplified using primers which bind to the 3' end of the Kappa or Lamda chain together with primers which anneal to the V kappa or V lambda leader sequence. The full length heavy and light chains can be generated and sequenced.

As used herein the term "C-terminus" refers to the extremity of a polypeptide, i.e. at the C-terminal end of the polypeptide, and is not to be construed as meaning in the general direction thereof. Likewise, the term "N-terminus" refers to the extremity of a polypeptide, i.e. at the N-terminal end of the polypeptide, and is not to be construed as meaning in the general direction thereof.

As used herein the term, the term "competitive immunoassay" refers to an immunoassay in which the target peptide present in a sample (if any) competes with known amount of target of peptide (which for example is bound to a fixed substrate or is labelled) for to binding an antibody, which is a technique known to those skilled in the art.

As used herein the term "ELISA" (enzyme-linked immunosorbent assay) refers to an immunoassay in which the target peptide present in a sample (if any) is detected using antibodies linked to an enzyme, such as horseradish peroxidase or alkaline phosphatase.

The activity of the enzyme is then assessed by incubation with a substrate generating a measurable product. The presence and/or amount of target peptide in a sample can thereby be detected and/or quantified. ELISA is a technique known to those skilled in the art.

As used herein the term "ECLIA" (Electrochemical linked immunosorbent assay) refers to an immunoassay in which the target peptide present in a sample (if any) is detected using antibodies linked to an electrochemiluminescent label, such as the SULFO-Tag system. Electricity is applied to the samples leading to light emission by the electrochemiluminescent labels. Light intensity is then measured to quantify the target peptide in the sample. The presence and/or amount of target peptide in a sample can thereby be detected and/or quantified. ECLIA is a technique known to those skilled in the art.

As used herein the term "amount of binding" refers to the quantification of binding between monoclonal antibody and target peptide, which said quantification is determined by comparing the measured values of target peptide in the biofluid samples against a calibration curve, wherein the calibration curve is produced using standard samples of known concentration of the target peptide. In the specific assay disclosed herein which measures in biofluids target peptides having the N-terminus amino acid sequence MGNTGPTGAV (SEQ ID No. 1), the calibration curve is produced using standard samples of known concentration of a calibration peptide having the N-terminus amino acid sequence MGNTGPTGAV (SEQ ID No. 1), (and which may in particular consist of the amino acid sequence MGNTGPTGAV (SEQ ID No. 1)). The values measured in the biofluid samples are compared to the calibration curve to determine the actual quantity of target peptide in the sample.

As used herein "Immunotherapy" refers to methods of artificially stimulating the immune system in the treatment of cancers. There are a number of different types of immunotherapy including but not limited to T-cell engagers, CAR T-cell therapy, Cytokines, and Immune checkpoint inhibitors. Preferably the immunotherapy comprises administering at least one immune checkpoint inhibitor such as ipilimumab, pembrolizumab, nivolumab, atezolizumab, avelumab, durvalumab, cemiplimab or combinations thereof. Preferably the immune checkpoint inhibitor is ipilimumab.

As used herein, the term "C4-aa$^{1355n}$" or "C4G" refers to type VI collagen α2 chain neo-epitope peptide having the N-terminal amino acid sequence MGNTGPTGAV (SEQ ID No. 1) produced by a protease which causes cleavage between amino acids $F^{1354}$ and $M^{1355}$. Preferably the protease is a serine protease, such as Granzyme B or a matrix metalloproteinase, such as MMP-9.

FIGURES

The invention will now be described in the examples below which refer to the following figures:

FIGS. 1A-1B show the specificity of the C4-aa$^{1355}$ monoclonal antibody

The monoclonal antibody's reactivity in the competitive C4-aa$^{1355}$ ECLIA was tested towards The selection peptide (MGNTGPTGAV (SEQ ID No. 1)), an elongated peptide (FMGNTGPTGAV (SEQ ID No. 7)), a truncated peptide (GNTGPTGAV (SEQ ID No. 3)), a non-sense selection peptide (LLARDFEKNY (SEQ ID No. 18)) and a non-sense coating peptide (LLARDFEKNY-K-biotin (SEQ ID No. 19)) (FIG. 1A) and the selection peptide (MGNTGPTGAV (SEQ ID No. 1)) and the deselections peptide 1 (MGQTGPTGAV (SEQ ID No. 4)), 2 (MGNSGPTGAV (SEQ ID No. 5)) and 3 (QGNTGPTGAV (SEQ ID No. 6)) (FIG. 1B). % B/B0: B equals the intensity of a sample well (OD at x ng/ml peptide) and B0 equals the maximum intensity (OD at 0 ng/ml peptide).

FIGS. 2A-2C show the Proteolytic degradation of type IV collagen α2 chain with MMP-9 or granzyme B Type IV collagen α2 chain was incubated with MMP-9 (A) or granzyme B (GzB) (B) for 72 hours and then C4-aa$^{1355}$ ECLIA levels were measured.

C4-aa$^{1355}$ levels in serum at baseline and 3 weeks after Ipilimumab treatment (n=41). Serum levels were compared using Wilcoxon matched-pairs rank test.

Figure 4A:
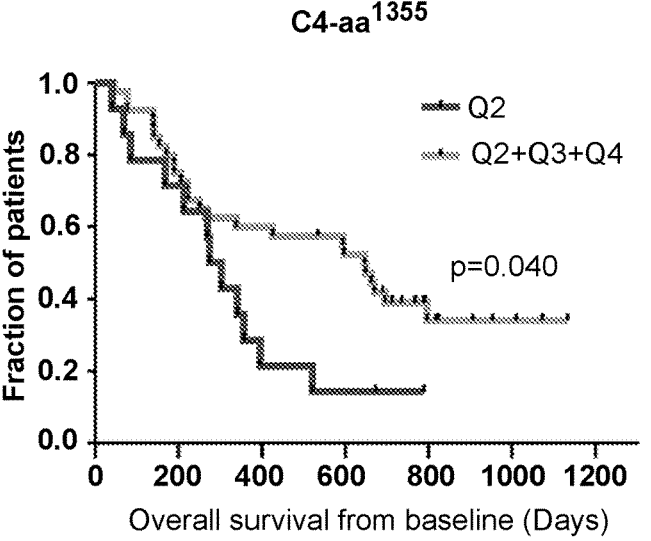
Figure 4B:
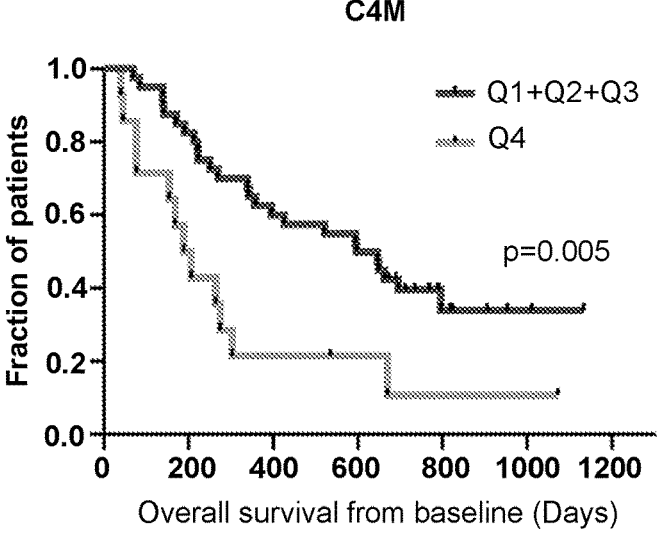

FIGS. 4A-4B show the Kaplan-Meier analysis of overall survival.

Overall survival for metastatic melanoma patients treated with Ipilimumab with pre-treatment levels in the upper quartiles (Q2+Q3+Q4) vs the lower quartile (Q1) for C4-aa$^{1355}$ (cut off value: 14.5 ng/ml) (FIG. 4A) while for C4M it is the upper quartile (Q4) vs the lower quartiles (Q1+Q2+Q3) (cut off value: 35.0 ng/ml) (B). A log-rank test was used to determine differences between the survival curves where p-value of p<0.05 was considered statistically significant.

Figure 5:
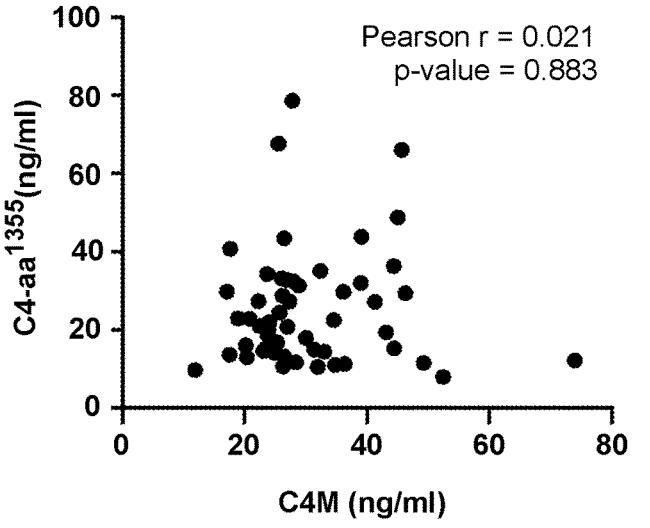

FIG. 5 shows the Correlation between C4-aa$^{1355}$ and C4M levels in metastatic melanoma patients Pearson's correlation analysis was performed to describe the relationship between C4-aa$^{1355}$ and C4M levels in pre-treatment serum from metastatic melanoma treated with Ipilimumab (n=54).

Figure 6A:
Figure 6A:
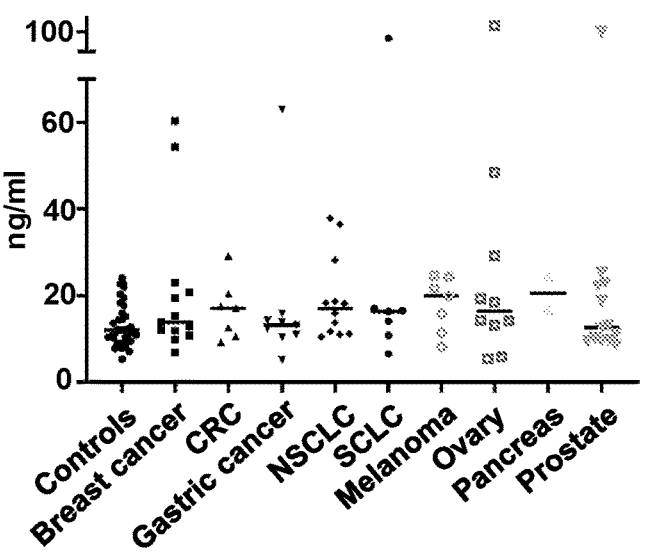
Figure 6B:
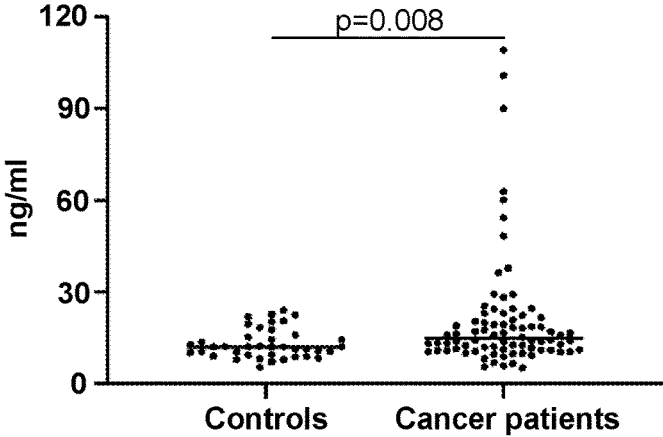
Figure 6C:
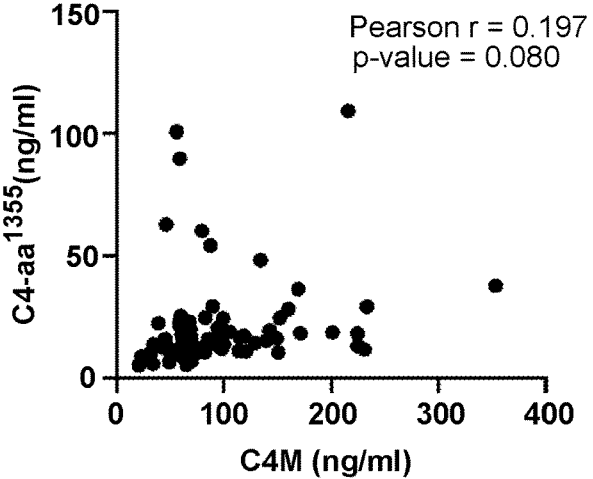

FIGS. 6A-6C show the Serum C4-aa$^{1355}$ levels in cancer patients and healthy controls.

FIG. 6A shows serum C4-aa$^{1355}$ levels in healthy controls (n=40), breast cancer (n=13), colorectal cancer (CRC) (n=7), gastric cancer (n=9), non-small cell lung cancer (NSCLC) (n=12), small cell lung cancer (SCLC) (n=7), melanoma (n=7), ovary cancer (n=10), pancreas cancer (n=2) and prostate cancer (n=13). Groups were compared using Kruskal-Wallis test adjusted for Dunn's multiple comparisons. In FIG. 6B) C4-aa$^{1355}$ levels in serum from the healthy controls (n=40) were compared to the combined group of cancer patients (n=80) using unpaired Mann-Whitney test. The black horizontal lines represent the median value of the patients measured in duplicates. In FIG. 6C) a Pearson's correlation analysis was performed to describe the relationship between C4-aa$^{1355}$ and C4M levels in serum from the combined group of cancer patients (n=80).

Figure 7:
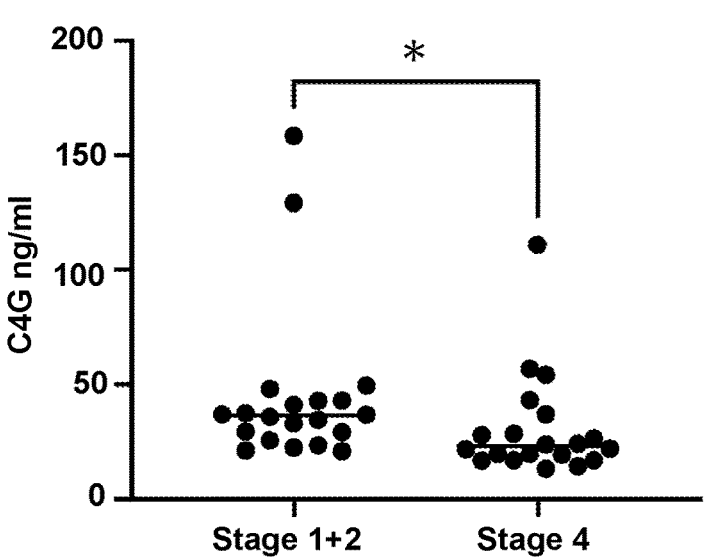

FIG. 7 shows serum C4G (C4-aa$^{1355}$) levels according to early and late stage pancreas ductal adenocarcinoma (PDAC). *p<0.05

Figure 8:
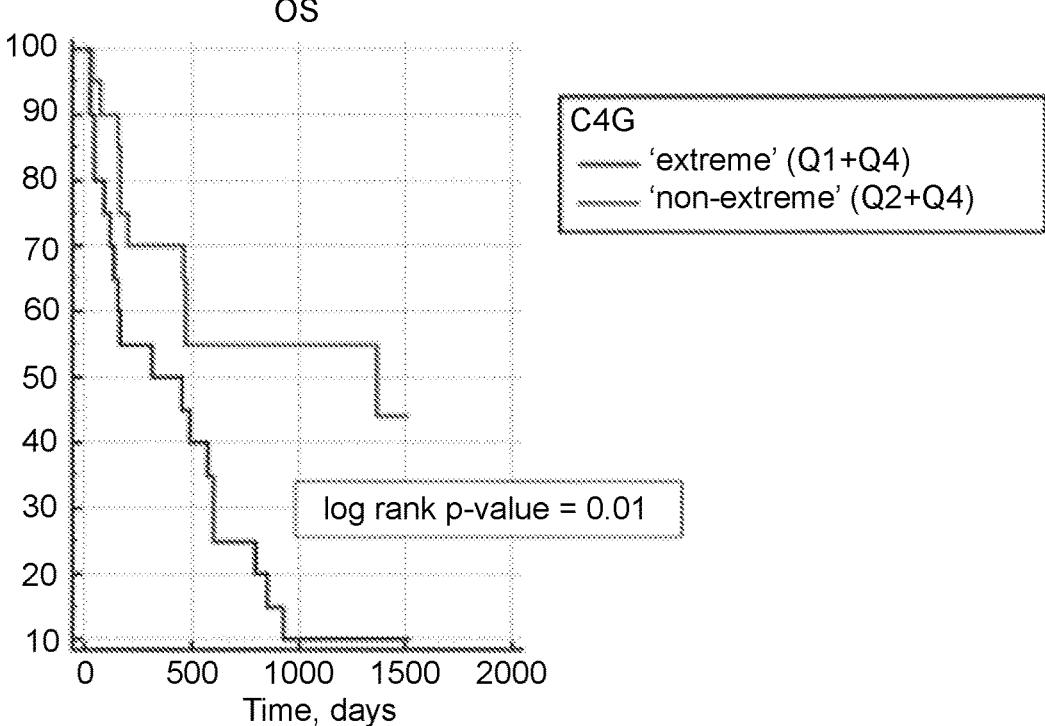

FIG. 8 shows Kaplan Meier plot for evaluating overall survival (OS) associated with C4G (C4-aa$^{1355}$) at baseline by grouping (dichotomizing) at the 25$^{th}$ percentile and 75$^{th}$ percentile (Q1+Q4 vs Q2+Q3)

EXAMPLES

Various embodiments are described and disclosed in the following Examples, which are set forth to aid in the understanding of the present disclosure and should not be construed to limit in any way the scope of the invention as defined in the claims which follow thereafter. The following examples are put forth so as to provide those of ordinary skill in the art with a complete disclosure and description of how to make and use the described embodiments, and are not intended to limit the scope of the present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

All reagents used for the experiments were standard chemicals from Merck (Whitehouse station, NJ, USA) and Sigma-Aldrich (St. Louis, MO, USA) unless otherwise stated.

Peptide Identification by Mass Spectrometry

Type IV collagen from human placenta (Sigma Aldrich, cat. no. C5533) was proteolytically digested in the ratio 10:1 at 37° C. for 24 and 72 hours and then stored at −80° C. until mass spectrometry analysis.

One µg of sample (corresponding to digested or undigested collagen in 100 µl 50 mM Tris, 150 mM NaCl, pH 7.5 buffer) was reduced by 10 mM dithiothreitol for 30 minutes at 56° C. and alkylated by 40 mM iodoacetamide for 60 minutes in the dark at room temperature. Any remaining iodoacetamide was quenched by 10 mM dithiothreitol for 5 minutes at room temperature. The samples digested with Lys-C at 1:20 enzyme:substrate ratio (Wako chemicals, cat #125-05061) for 16 hours on a shaker at 37° C. After addition of 100 µl 1 M NaCl with 1% formic acid to the digests, these were run through 30 kDa filters (PALL Life Sciences, cat #OD030C34) to remove GAGs and desalted with reversed-phase Vydac UltraMicro Spin C18 columns (Harvard Apparatus, cat #74-7206) according to the manufacturer's instructions. Non-targeted mass spectrometry analysis was performed on a quadrupole Orbitrap benchtop mass spectrometer, QExactive, (Thermo Scientific) equipped with an Easy nano-LC 1000 system (ThermoFisher Scientific). Separation was performed on 75 µm×25 cm, Acclaim Pepmap™ RSLC C18 capillary columns packed with 2 µm particles (ThermoFisher Scientific). A spray voltage of +2000 V was used with a heated ion transfer setting of 275° C. for desolvation. The on-line reversed-phase separation was performed using a flow rate of 300 nl/min and a linear binary gradient 85 min was used. The gradient started with 3% solvent B for 4 minutes, then going to 35% solvent B in 64 minutes, after which it goes to 45% solvent B in 5 minutes. Finally, the organic solvent concentration was increased up to 90% in 5 minutes and kept at 90% for 7 minutes. An MS scan (400-1200 m/z) was recorded in the Orbitrap mass analyzer set at a resolution of 70,000 at 200 m/z, $1\times10^6$ automatic gain control (AGC) target and 100 ms maximum ion injection time. The MS was followed by data-dependent collision-induced dissociation MS/MS scans at a resolution of 17,500 on the 15 most intense multiply charged ions at $2\times10^4$ intensity threshold, 2 m/z isolation width and dynamic exclusion enabled for 30 s. Identification from discovery data was performed using the *Homo sapiens* proteome (UniProt proteome ID UP000005640) with Proteome Discoverer 2.1 software (ThermoFisher Scientific). The processing workflow consisted of the following nodes: Spectrum Selector for spectra pre-processing (precursor mass range: 300-30000 Da; S/N Threshold: 1.5), Sequest-HT search engine (Protein Database: see above; Enzyme: Lys-C (semi); Max. missed cleavage sites: 2; Peptide length range 6-144 amino acids; Precursor mass tolerance: 10 ppm; Fragment mass tolerance: 0.02 Da; Static modification: cysteine carbamidomethylation; and Percolator for peptide validation (FDR<1% based on peptide q-value). Results were filtered to keep only the Master protein with at least one unique peptide, and protein grouping was allowed according to the parsimony principle. For label-free quantification (LFQ), the sum of the top 3 peptides for each protein was taken to reflect the intensity of the protein. Peptide intensities were quantified using a proprietary algorithm developed in Proteome Discoverer 2.1 (ThermoFisher Scientific).

Selection of Peptides

The first six amino acids from the N-terminal and C-terminal of each peptide from type IV collagen identified by mass spectrometry were regarded as a protease generated neo-epitope. The protease generated sequences were analyzed for homology to other human proteins and species using the NPS@: Network Protein Sequence Analysis with the Uniprot/Swiss-Prot database (16). The amino acid sequence C-terminal from the cleavage site $F^{1354}\downarrow M^{1355}$ ($^{1355}$MGNTGPTGAV$^{1364}$) was found unique for human type IV collagen α2 chain and selected as target for antibody production. Synthetic peptides used for monoclonal antibody production and technical evaluation of the ECLIA measuring protease mediated degradation of type IV collagen (C4-aa$^{1355}$) were purchased from Genscript and shown in table 1.

TABLE 1

| Synthetic peptides used for C4-aa$^{1355}$ assay development and validation | | |
| --- | --- | --- |
| Peptide | Amino acid sequence | SEQ ID No. |
| Selection peptide | $^{1355}$.MGNTGPTGAV$^{1364}$ | 1 |
| Immunogenic peptide | MGNTGPTGAV-GGC-KLH | 20 |
| Biotinylated coating peptide | MGNTGPTAV-K-biotin | 21 |
| Elongated peptide | FMGNTGPTGAV | 7 |

TABLE 1-continued

| Synthetic peptides used for C4-aa$^{1355}$ assay development and validation | | |
| --- | --- | --- |
| Peptide | Amino acid sequence | SEQ ID No. |
| Truncated peptide | GNTGPTGAV | 3 |
| Non-sense selection peptide | LLARDFEKNY | 18 |
| Non-sense coating peptide | LLARDFEKNY-K-biotin | 19 |
| Deselection 1 | MGQTGPTGAV | 4 |
| Deselection 2 | MGNSGPTGAV | 5 |
| Deselection 3 | QGNTGPTGAV | 6 |

KLH, Keyhole Limpet Hemocyanin

The target sequence was used as the selection peptide (MGNTGPTGAV (SEQ ID No. 1)). The immunogenic peptide (MGNTGPTGAV-GGC-KLH (SEQ ID No. 20)) was generated by covalently linking the selection peptide to Keyhole Limpet Hemocyanin (KLH) carrier protein with addition of glycine and cysteine residues in between to ensure right linking. A biotinylated peptide (MGNTGPTAV-K-biotin (SEQ ID No. 21)) was used as a coating peptide. The specificity of the antibody was tested by including an elongated peptide (FMGNTGPTGAV (SEQ ID No. 7)), a truncated peptide (GNTGPTGAV (SEQ ID No. 3)), a non-sense selection peptide (LLARDFEKNY (SEQ ID No. 18)) and a non-sense coating peptide (LLARDFEKNY-K-biotin (SEQ ID No. 19)). To test for potential cross-reactivity to other ECM proteins with similar sequences, three peptides with one amino acid mismatch at either position one (QGNTGPTGAV (SEQ ID No. 6)), three (MGQTGPTGAV (SEQ ID No. 4)) or four (MGNSGPTGAV (SEQ ID No. 5)) from the N-terminal were included in the specificity test. Antibody specificity was calculated as percentage of signal inhibition of two-fold diluted peptides.

Monoclonal Antibody Production and Clone Characterization

Female Balb/C mice of 6-7 weeks of age were immunized subcutaneously with 200 μl emulsified antigen containing 100 μg immunogenic peptide (MGNTGPTGAV-GGC-KLH) with Stimune Immunogenic adjuvant (Thermo fisher, cat. no. 7925000) repeatedly every second week until stable titer levels were obtained. The mouse with the highest antibody titer rested for four weeks and was then boosted intraperitoneally with immunogenic peptide. After three days, splenocytes were isolated and fused with murine SP2/0 myeloma cells to produce hybridoma cells as previously described (17). The hybridoma cells were cultured in 96-well microtiter plates and limited dilution was used to secure monoclonal growth. Supernatants from the monoclonal antibody producing hybridoma cells were screened for reactivity against the selection peptide and human serum samples in a preliminary competitive ELISA using biotinylated coating peptide on streptavidin-coated microtiter plates (Roche, cat. no. 11940279). The clone with the best reactivity towards the selection peptide was purified using protein-G-columns according to the manufacturer's instructions (GE Healthcare Life Sciences, cat. no. 17-0404-01).

C4-aa$^{1355}$ ECLIA Protocol

During assay development, an optimal incubation buffer, time, temperature and concentrations of antibody and coating peptide were determined and the finalized competitive C4-aa$^{1355}$ ECLIA protocol was as follows: A MSD GOLD 96-well streptavidin pre-coated plate (Meso Scale Discovery, cat. no. L15SA-1) was incubated with 150 µl/well blocking buffer (10 mM phosphate-buffered saline (PBS) with bovine serum albumin (BSA) (5% w/v) and bronidox (0.36% v/v), 8 g/L NaCl, pH 7.4) for 60 minutes at 20° C. with shaking (300 rpm) in darkness. The plate was coated with 25 µl/well biotinylated coating peptide dissolved in assay buffer (50 mM PBS with BSA (1% w/v), Tween-20 (0.1% w/v) and bronidox (0.36% v/v), 8 g/L NaCl, pH 7.4) to a concentration at 2 ng/ml and incubated for 60 minutes at 20° C. with shaking (750 rpm) in darkness. Next, 25 µl/well selection peptide, assay controls or pre-diluted serum/plasma sample (1:2) were added followed by immediately addition of 25 µl/well of SULFO-TAG (MSD GOLD SULFO-TAG NHS-Ester Conjugation, Meso Scale Discovery, cat. no. R31AA-1) labelled monoclonal antibody diluted in assay buffer to a final concentration at 25 ng/ml and the plate incubated 20 hours at 4° C. with shaking (300 rpm) in darkness. All incubation steps were followed by washing the plate three times in washing buffer (20 mM Tris, 50 mM NaCl, pH 7.2). Finally, 150 µl/well of MSD GOLD Read Buffer (Meso Scale Discovery, cat. no. R92TG-2) was added and the plate was read immediately within 2 minutes in a Sector Imager 6000 (Meso Scale Discovery). SULFO-TAG enabled light emission when electricity was applied, and the light emission data was analyzed using the MSD Discovery Workbench 4.0 software. The analyte concentration was calculated using a 4-parametric curve fit model.

Technical Evaluation of the C4-aa$^{1355}$ Assay

The lower limit of detection was determined from ten independent runs using the mean of the background plus 2.5 times the standard deviation. The upper limit of detection was determined from the same ten runs using the back-calibration concentration of the selection peptide at highest concentration minus 2.5 times the standard deviation. The intra- and inter-assay variation were determined by ten independent runs of seven samples in duplicates with concentrations covering the entire linear range of the standard curve. The samples consisted of four samples with different amount of selection peptide in assay buffer and three different healthy human serum samples. Intra-assay variation was calculated as the mean coefficient of variance (CV %) within plates and the inter-assay variation was calculated as the mean CV % between the ten plates. To determine linearity of the assay, two-fold dilutions of human serum (n=3) or EDTA plasma samples (n=3) were performed and the linearity was calculated as a percentage recovery of undiluted sample. Analyte stability was tested by four repeated freeze/thaw cycles of human serum (n=3 at each cycle) and the analyte recovery was calculated with the first cycle as reference. Analyte stability was furthermore tested by incubated human serum samples (n=3 at each time point) at 4° C. or 20° C. for 24 or 48 hours and recovery was calculated with samples stored at −20° C. as reference. Interference was tested by adding a low/high content of biotin (3.0/9.0 ng/ml), lipemia (1.5/5.0 mg/ml) and hemoglobin (2.5/5.0 mg/ml) to a serum sample and the recovery was calculated with the serum sample as reference.

Cleavage of Type IV Collagen In Vitro

Recombinant type IV collagen α2 chain (MyBioSource) and MMP-9 (Giotto, cat. no. G04MP09C) or granzyme B (GzB) (Abcam, cat. no. ab168093) were incubated 10:1 (10 µg type IV collagen and 1 µg protease) in MMP-buffer (50 mM Tris-HCl, 150 nM NaCl, 10 mM CaCl$_2$, 10 µM ZnCl, 0.05% Brij35, pH 7.5) or GzB buffer (50 mM Tris, 150 mM NaCl, pH 7.5), respectively, at 37° C. for 72 hours and then stored at −80° C. until analysis. Digestion of carboxymethylated transferrin with MMP-9 or GzB were included as positive controls, and MMP buffer added MMP-9 alone, and GzB buffer added GzB alone were included as negative controls. The activity of MMP-9 and GzB was confirmed by Coomassie blue staining (Data not shown).

Clinical Validation of the C4-aa$^{1355}$ Assay

Serum samples were collected from stage IV melanoma patients (n=54) treated with Ipilimumab (3 mg/kg body weight) as standard of care at Herlev Hospital and Aarhus University Hospital, Denmark subsequent to informed consent. The study was approved by the Ethics Committee for The Capital Region of Denmark (H-2-2012-058) in compliance with the Helsinki Declaration of 1975. Serum samples were collected at baseline and 3 weeks after the first treatment (before the 2$^{nd}$ dose of treatment).

Serum samples from other cancer patients were obtained from the commercial vendor Asterand Bioscience (Detroit, MI, USA) and included breast cancer (n=13), colorectal cancer (CRC) (n=7), gastric cancer (n=9), non-small cell lung cancer (NSCLC) (n=12), small cell lung cancer (SCLC) (n=7), melanoma (n=7), ovary cancer (n=10), pancreas cancer (n=2) and prostate cancer (n=13). Serum samples from healthy controls (n=40) were obtained from the commercial vender Valley BioMedical (Winchester, VA, USA). The samples were collected after informed content and approval by appropriate Institutional Review Board in compliance with the Helsinki Declaration.

C4M was assessed in serum samples from the cancer patients for comparison to the new developed biomarker C4-aa$^{1355}$. The C4M competitive ELISA is a well-characterized assay based on a monoclonal antibody specific towards a neo-epitope of MMP-9 mediated degradation of type IV collagen manufactured by Nordic Bioscience (Herlev, Denmark) and measurements were performed according to the manufacturer's specifications (18).

Statistical Analyses

Wilcoxon matched pairs signed rank test was used to compare biomarker levels in melanoma patients at baseline with week 3. Kaplan-Meier survival curves were used to analyze overall survival (OS) in melanoma patients with pre-treatment levels in the upper quartiles (Q2+Q3+Q4) vs the lower quartile (Q1) for C4-aa$^{1355}$ while it for C4M is the upper quartile (Q4) vs the lower quartiles (Q1+Q2+Q3).

The levels of C4-aa$^{1355}$ in serum samples from the different cancer patients were compared to healthy controls using Kruskal-Wallis test adjusted for Dunn's multiple comparisons. The healthy controls were compared to the combined group of cancer patients using unpaired Mann-Whitney test. Pearson's correlation analysis was performed to describe the relationship between C4-aa$^{1355}$ and C4M levels in serum from the metastatic melanoma and combined group of cancer patients, respectively. A p-value of p<0.05 was considered statistically significant. Graphs and statistical analyses were performed using GraphPad Prism version 7 (GraphPad Software, CA, USA).

Results

Specificity of the Novel C4-Aa$^{1355}$ Assay

Figure 1A:
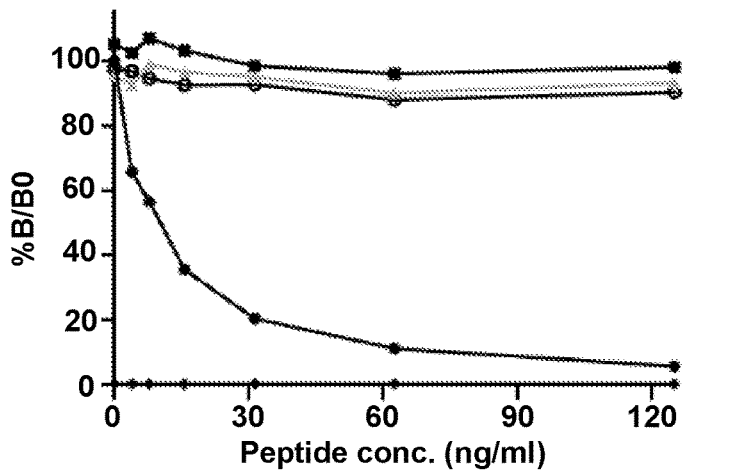
Figure 1B:
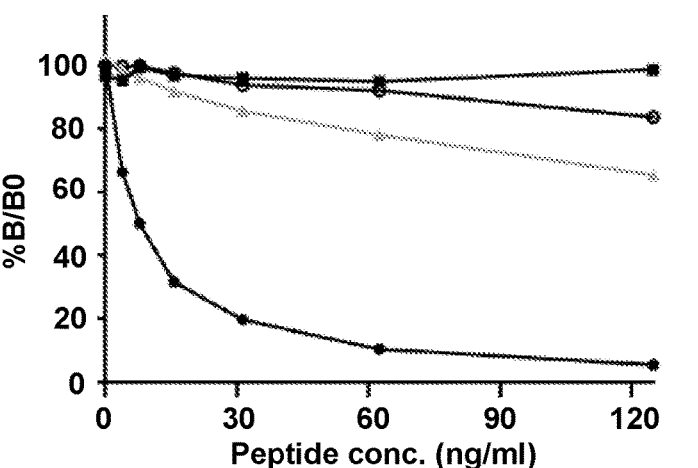

The specificity of the monoclonal antibody in the new competitive C4-aa$^{1355}$ ECLIA was tested. The selection peptide inhibited the signal in a dose-dependent manner whereas the elongated, truncated and non-sense selection peptide did not inhibit the signal (FIG. 1A). No signal was observed when using a non-sense biotinylated peptide (FIG. 1A). When the reactivity was tested towards peptides with only one amino acid mismatch compared to the selection peptide, no reactivity was detected in peptide concentrations 0-30 ng/ml whereas deselection peptide 2 inhibited the signal to 65% at the highest concentration (FIG. 1B). Together, these data suggest that the monoclonal antibody is highly specific to the neo-epitope on the selection peptide. Proteolytic Degradation of Type IV Collagen by MMP-9

Figure 2A:
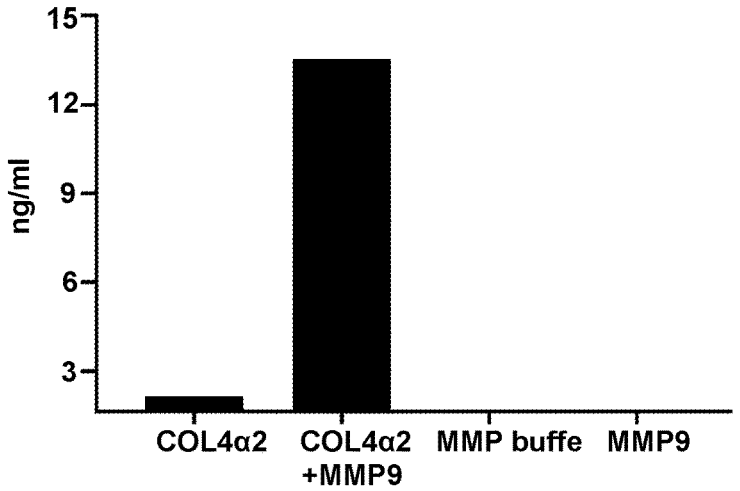
Figure 2B:
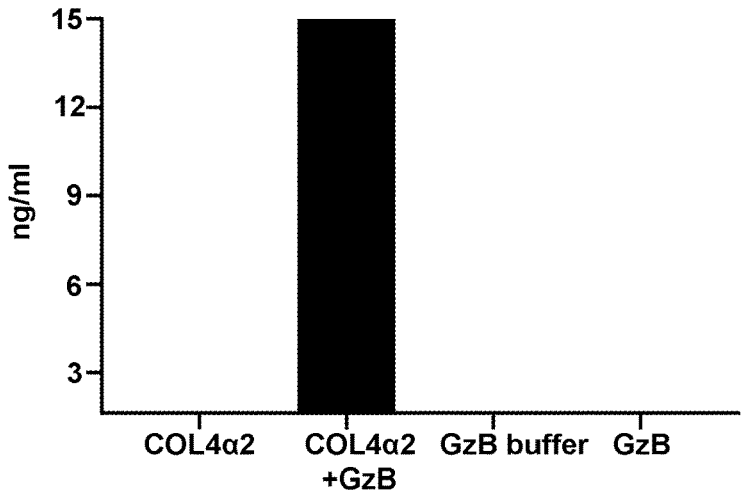

To confirm that the C4-aa[1355] antibody/assay recognized a protease generated type IV collagen neo-epitope, C4-aa[1355] was measured in non-digested, MMP-9 digested and GzB digested type IV collagen. As shown in FIGS. 2A-2C, C4-aa[1355] was detectable only in MMP-9 digested and GzB digested samples whereas no levels were detected in undigested (without protease) samples indicating that the antibody is specific for the protease generated neo-epitope. Technical Evaluation of the C4-aa[1355] Assay Technical performance of the C4-aa[1355] ECLIA assay was further evaluated through the different technical validation steps summarized in Table 2. The detection range of the assay was 0.6-832 ng/ml. The intra- and inter-assay variations were 6% and 8%, and below the acceptance criterion on 10% and 15%, respectively. Linearity was detected from undiluted to a 1:4 dilution with dilution recoveries at 94% and 106% for serum and EDTA plasma, respectively. After 4 freeze/thaw cycles, the analyte recovery in serum was 96%. After prolonged storage of human serum at 4° C. or 20° C. for 48 hours, the analyte recoveries were 122% and 109%, respectively. No interference was detected from low or high contents of lipemia or hemoglobin in serum with recoveries ranging from 92-111%. Low content of biotin neither interfered with the analyte whereas high content of biotin did with recoveries at 94% and 71%, respectively. The acceptance criterion of the recoveries was within 100±20%. Together, these results indicate that the C4-aa[1355] ECLIA is a technical robust assay.

TABLE 2

Technical validation of the C4-aa[1355] assay

| Technical validation step | Results |
|---|---|
| Detection range | 0.6-832 ng/ml |
| Intra-assay variation | 6% |
| Inter-assay variation | 8% |
| Dilution recovery of serum | 94% |
| Dilution recovery of EDTA plasma | 106% |
| Analyte recovery, 4 freeze/thaw cycles | 96% |
| Analyte recovery 24 h, 4° C./20° C. | 109%/106% |
| Analyte recovery 48 h, 4° C./20° C. | 122%/109% |
| Interference test | |
| Biotin recovery, low/high | 94%/71% |
| Lipemia recovery, low/high | 111%/102% |
| Hemoglobin recovery, low/high | 99%/92% |

Percentages are reported as mean

Figure 3:
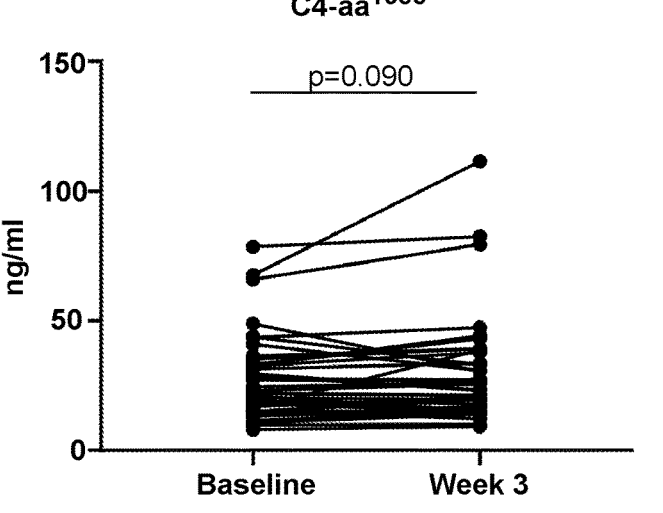
FIG. 3 shows the Serum C4-aa$^{1355}$ levels in metastatic melanoma patients.

Clinical Evaluation of the C4-Aa[1355] Assay in Ipilimumab Treated Metastatic Melanoma Patients To evaluate the biomarker potential of C4-aa[1355], C4-aa[1355] was measured in serum from metastatic melanoma patients at baseline and 3 weeks after Ipilimumab treatment. When the biomarkers levels were paired, C4-aa[1355] levels were slightly elevated 3 weeks after treatment (p=0.090) (FIG. 3).

Next, the association between the C4-aa[1355] biomarker and survival outcomes were evaluated by Kaplan-Meier curves. High baseline levels (Q2+Q3+Q4) of C4-aa[1355] were significantly associated with longer overall survival (OS) compared to low levels (Q1) (p=0.040) (FIG. 4A). The median OS was 646 days in biomarker high patients versus 290 days in biomarker low patients.

As the C4-aa[1355] and C4M biomarker measure two different protease generated neo-epitopes on type IV collagen, the association between C4M and OS was also evaluated. These findings on C4M have previously published [8] and the results for C4M measured in the 54 patients are shown in FIG. 4B. For the C4M biomarker, high baseline levels (Q4) were significantly associated with shorter OS compared to low levels (Q1+Q2+Q3) (p=0.005) (FIG. 4B). Interestingly, the two biomarkers showed opposite associations to outcome.

Furthermore, the correlation between the C4-aa[1355] and C4M levels in the metastatic melanoma patients at baseline were investigated. C4-aa[1355] and C4M did not correlate (r=0.021, p=0.883) (FIG. 5).

Clinical Evaluation of the C4-aa[1355] Assay in Other Cancer Patients

To further evaluate the biomarker potential of C4-aa[1355], it was measured in serum from different cancer patients with either breast cancer, CRC, gastric cancer, NSCLC, SCLC, melanoma, ovary cancer, pancreas cancer or prostate cancer and in serum from healthy controls. Inter-patient variations in the C4-aa[1355] biomarker levels in each group of patients (FIG. 6A) were observed. When comparing the median C4-aa[1355] levels in healthy controls to each group of cancer patients, no significant differences were observed (FIG. 6A). However, when comparing C4-aa[1355] in healthy controls to the combined group of cancer patients, C4-aa[1355] levels were significantly elevated in cancer patients (14.8 ng/ml) compared to healthy controls (12.0 ng/ml) (p=0.006) (FIG. 6B).

As shown in the first cohort, again C4-aa[1355] and C4M levels in these cancer patients, did not correlate (r=0.197, p=0.080) (FIG. 6C).

Serum C4-aa[1355] (C4G) Measured at Baseline Predicts Outcome in Pancreas Ductal Adenocarcinoma (PDAC) Patients Treated with Chemotherapy C4-aa[1355] (C4G) was measured in pretreatment serum samples from 40 patients with pancreas ductal adenocarcinoma (PDAC). All patients were from the Danish BIOPAC study "BIOmarkers in patients with Pancreatic Cancer" (NCT03311776). Patients were recruited from six Danish hospitals from December 2008 until September 2017. PDAC patients had histologically confirmed tumors. The PDAC patients were treated with various types of chemotherapy according to national guidelines (gicancer.dk). The study was carried out in accordance with the recommendations of the Danish Regional Committee on Health Research Ethics. The BIOPAC protocol was approved by the Danish Regional Committee on Health Research Ethics (VEK ref. KA-20060113) and the Data Protection Agency (j.nr.2006-41-6848). All subjects gave written informed consent in accordance with the Declaration of Helsinki, version 8. Blood samples were obtained at the time of diagnosis or before operation. Samples were processed according to nationally approved blood standard operating procedures for (herlevhospital.dk/biopac.dk). Serum samples and clinical data from patients were collected prospectively. Serum sample were measured blinded.

Results are shown according to stage of disease in FIG. 7. C4-aa[1355] was significantly lower in serum from patients with late stage vs early stage of PDAC (Mann Whitney test, p-value=0.0132). The possible association with C4-aa[1355] at baseline and overall survival (OS) in PDAC was evaluated. Using the $25^{th}$ percentile and $75^{th}$ percentile cut point to define a group with 'extreme' C4-aa[1355] levels (<$25^{th}$ percentile+>75$^{th}$ percentile, i.e. quartile 1 and quartile 4, Q1+Q4) and Kaplan Meier analysis, patients with 'non-extreme' levels of C4-aa$^{1355}$ (>25$^{th}$ percentile to <75$^{th}$ percentile, Q2+Q3) were found to have improved overall survival (FIG. 8). In support univariate Cox regression analysis shown a reduced risk of dying in the subgroup of patients with 'non-extreme' C4-aa$^{1355}$ levels (Table 3). Moreover, multivariate cox regression analysis showed that the predictive value of C4-aa$^{1355}$ was independent of stage.

TABLE 3

Cox regression analysis for predicting overall survival outcome

|  | HR | 95% CI | p-value |
|---|---|---|---|
| Univariate analysis |  |  |  |
| C4-aa$^{1355}$, Q2 + Q3 vs Q1 + Q4 | 0.37 | 0.17-0.81 | 0.0131 |
| Multivariate analysis adjusted for stage of disease (early vs late) |  |  |  |
| C4-aa$^{1355}$, Q2 + Q3 vs Q1 + Q4 | 0.38 | 0.17-0.85 | 0.0179 |

Discussion and Conclusions

A robust and specific competitive ECLIA that enables non-invasive measurement of a neo-epitope generated by protease mediated degradation of type IV collagen (C4-aa$^{1355}$) has been developed and validated. High baseline levels of C4-aa$^{1355}$ in these melanoma patients were associated with clinical response (longer overall survival) to immune checkpoint inhibitor treatment. On the contrary, high baseline levels of C4M were associated with shorter overall survival. C4-aa$^{1355}$ and C4M levels in these samples did not correlate. C4-aa$^{1355}$ and C4M both measure a neo-epitope on type IV collagen but at two different sites, and interestingly these data suggest that these different cleavage products are released during two different pathologically events, one being associated with good outcome and one being associated with poor outcome when measured at baseline. Moreover, 3 weeks after immune checkpoint inhibitor treatment slightly elevated levels of C4-aa$^{1355}$ were detected in serum from the metastatic melanoma patients compared to baseline.

The finding that C4-aa$^{1355}$ associates with clinical response to immune checkpoint inhibitor treatment in these melanoma patients indicates that the C4-aa$^{1355}$ assay has a biomarker potential in the immuno-oncology setting to identify cancer patients with a T-cell permissive tumor microenvironment responding to treatment. C4-aa$^{1355}$ may reflect protease mediated T-cell transmigration from the circulation to the underlying stroma. Conversely, C4M associates with poor response supporting previous findings suggesting that C4M is linked to tumor activity and a reactive stroma (8-10).

Interestingly, this study indicates that one type of type IV collagen neo-epitope fragment is associated to tumorigenesis (C4M) and another type of type IV collagen neo-epitope fragment is associated to T-cell infiltration (C4-aa$^{1355}$) supporting the value of measuring pathological specific neo-epitopes and not just the total protein.

C4-aa$^{1355}$ was also elevated in other cancer types than melanoma suggesting that the biomarker has a potential in other indications. Furthermore, there was again no correlation between C4-aa$^{1355}$ and C4M levels in these cancer patients verifying that these biomarkers reflect pathologically distinct aspect of the tumor microenvironment.

C4-aa$^{1355}$ was found to be elevated in patient with early stage pancreas ductal adenocarcinoma (PDAC). In addition, those patients with an extreme level of the marker C4-aa$^{1355}$ (i.e. in the 1st or 4th quartile) were found to have a reduced overall survival rate.

To our knowledge, this is the first study to show that this specific protease mediated degradation of type IV collagen (C4-aa$^{1355}$) has biomarker potential in cancer and is associated with response to immune checkpoint inhibitor therapy.

REFERENCES

1. Thallinger C, Füreder T, Preusser M, Heller G, Müllauer L, Höller C, et al. Review of cancer treatment with immune checkpoint inhibitors: Current concepts, expectations, limitations and pitfalls. Wiener Klinische Wochenschrift. 2018.
2. Chen D S, Mellman I. Elements of cancer immunity and the cancer-immune set point. Nature [Internet]. 2017; 541 (7637): 321-30.
3. Trujillo J A, Sweis R F, Bao R, Luke J J. T cell-inflamed versus Non-T cell-inflamed tumors: a conceptual framework for cancer immunotherapy drug development and combination therapy selection. Cancer Immunology Research. 2018;
4. Salmon H, Franciszkiewicz K, Damotte D, Dieu-Nosjean M C, Validire P, Trautmann A, et al. Matrix architecture defines the preferential localization and migration of T cells into the stroma of human lung tumors. Journal of Clinical Investigation. 2012; 122(3):899-910.
5. Nissen N I, Karsdal M, Willumsen N. Collagens and Cancer associated fibroblasts in the reactive stroma and its relation to Cancer biology. Journal of Experimental and Clinical Cancer Research. 2019.
6. Chakravarthy A, Khan L, Bensler N P, Bose P, De Carvalho D D. TGF-β-associated extracellular matrix genes link cancer-associated fibroblasts to immune evasion and immunotherapy failure. Nature Communications. 2018;
7. Mariathasan S, Turley S J, Nickles D, Castiglioni A, Yuen K, Wang Y, et al. TGFβ attenuates tumour response to PD-L1 blockade by contributing to exclusion of T cells. Nature. 2018;
8. Jensen C, Madsen D H, Hansen M, Schmidt H, Svane I M, Karsdal M A, et al. Non-invasive biomarkers derived from the extracellular matrix associate with response to immune checkpoint blockade (anti-CTLA-4) in metastatic melanoma patients. Journal for ImmunoTherapy of Cancer. 2018;
9. Kehlet S N, Sanz-Pamplona R, Brix S, Leeming D J, Karsdal M A, Moreno V. Excessive collagen turnover products are released during colorectal cancer progression and elevated in serum from metastatic colorectal cancer patients. Scientific Reports [Internet]. 2016; 6 (1): 30599.
10. Bager C L, Willumsen N, Leeming D J, Smith V, Karsdal M A, Dornan D, et al. Collagen degradation products measured in serum can separate ovarian and breast cancer patients from healthy controls: A preliminary study. Cancer Biomarkers. 2015; 15(6):783-8.
11. Prakash M D, Munoz M A, Jain R, Tong P L, Koskinen A, Regner M, et al. Granzyme B promotes cytotoxic lymphocyte transmigration via basement membrane remodeling. Immunity. 2014;
12. St-Pierre Y, Potworowski E F. T cell control of extracellular matrix degradation. Developmental Immunology. 2000;

13. El-Shabrawi Y, Walch A, Hermann J, Egger G, Foster C S. Inhibition of MMP-dependent chemotaxis and amelioration of experimental autoimmune uveitis with a selective metalloproteinase-2 and -9 inhibitor. Journal of Neuroimmunology. 2004;

14. Leppert D, Hauser S L, Kishiyama J L, An S, Zeng L, Goetzl E J. Stimulation of matrix metalloproteinase-dependent migration of T cells by eicosanoids. FASEB Journal. 1995;

15. Edsparr K, Basse P H, Goldfarb R H, Albertsson P. Matrix metalloproteinases in cytotoxic lymphocytes impact on tumour infiltration and immunomodulation. Cancer Microenvironment. 2011.

16. Combet C, Blanchet C, Geourjon C, Deléage G. NPS@: network protein sequence analysis. Trends in biochemical sciences. 2000 March; 25(3):147-50.

17. Gefter M L, Margulies D H, Scharff M D. A simple method for polyethylene glycol-promoted hybridization of mouse myeloma cells. Somatic Cell Genetics. 1977; 3(2):231-6.

18. Sand J M, Larsen L, Hogaboam C, Martinez F, Han M, Larsen M R, et al. MMP mediated degradation of type IV collagen alpha 1 and alpha 3 chains reflects basement membrane remodeling in experimental and clinical fibrosis—Validation of two novel biomarker assays. PLoS ONE. 2013; 8(12).

19. Kabat, E. A., T. T. Wu, H. M. Perry, K. S. Gottesman and C. Foeller (1987), Sequences of Proteins of Immunological Interest, United States Department of Health and Human Services, Bethesda, Md., p. 1

---

The invention claimed is:

1. A monoclonal antibody that specifically recognises and binds to a peptide having the N-terminus amino acid sequence MGNTGPTGAV (SEQ ID NO: 1); wherein the monoclonal antibody comprises complement determining region (CDR) sequences:

```
CDR-L1:
                                (SEQ ID NO. 8)
KSSQSLLYSDGKTYLN,

CDR-L2:
                                (SEQ ID NO. 9)
LVSKLDS,

CDR-L3:
                                (SEQ ID NO. 10)
WQGTHFVT,

CDR-H1:
                                (SEQ ID NO. 11)
TYNIGVG,

CDR-H2:
                                (SEQ ID NO. 12)
HIWYNDIKYYNTALKS, and

CDR-H3:
                                (SEQ ID NO. 13)
LRPDSFDY.
```

2. The monoclonal antibody of claim 1, wherein the monoclonal antibody is a monoclonal antibody raised against a synthetic peptide having the N-terminus amino acid sequence MGNTGPTGAV (SEQ ID NO. 1).

3. The monoclonal antibody of claim 1, wherein the monoclonal antibody does not specifically recognise or bind to a peptide having the N-terminus amino acid sequence selected from the group consisting of XMGNTGPTGAV (SEQ ID No. 2), wherein X represents any amino acid, GNTGPTGAV (SEQ ID NO. 3), MGQTGPTGAV (SEQ ID NO. 4), MGNSGPTGAV (SEQ ID NO. 5), and QGNTGPTGAV (SEQ ID NO. 6).

4. A method for identifying if a subject with cancer will respond to immunotherapy, said method comprising detecting the presence of a peptide having the N-terminus amino acid sequence MGNTGPTGAV (SEQ ID NO. 1); wherein said detecting comprises contacting a sample from said subject with the monoclonal antibody of claim 1.

5. The method of claim 4, further comprising predicting survival outcome of the subject with cancer.

6. The method of claim 4, wherein said method is an immunoassay and comprises contacting a biofluid sample obtained from the subject with a monoclonal antibody that specifically recognises and binds to a peptide having the N-terminus amino acid sequence MGNTGPTGAV (SEQ ID NO. 1), and detecting binding between the monoclonal antibody and peptides in the sample.

7. The method of claim 6, wherein the detection is quantitative.

8. The method of claim 6, wherein the immunoassay is a competitive immunoassay.

9. The method of claim 6, wherein the monoclonal antibody is a monoclonal antibody raised against a synthetic peptide having the N-terminus amino acid sequence MGNTGPTGAV (SEQ ID NO. 1).

10. The method of claim 6, wherein the monoclonal antibody does not specifically recognise or bind to a peptide having the N-terminus amino acid sequence selected from the group consisting of XMGNTGPTGAV (SEQ ID No. 2), wherein X represents any amino acid, GNTGPTGAV (SEQ ID NO. 3), MGQTGPTGAV (SEQ ID NO. 4), MGNSGPTGAV (SEQ ID NO. 5), and QGNTGPTGAV (SEQ ID NO. 6).

11. The method of claim 4, wherein the subject has been diagnosed with a cancer selected from the group consisting of melanoma, breast, colorectal, gastric, non-small cell lung cancer, small cell lung cancer, ovarian, prostate and pancreatic cancer.

12. The method of claim 11, wherein the subject has been diagnosed with a melanoma, preferably metastatic melanoma.

13. The method of claim 4, wherein the method further comprises correlating the amount of said peptide with values associated with normal healthy subjects and/or values obtained from cancer patients who have responded to immunotherapy.

14. The method of claim 13, wherein the method further comprises administering immunotherapy to the subject that has an elevated level of the peptide present.

15. The method of claim 4, wherein said immunotherapy comprises at least one immune checkpoint inhibitor.

16. The method of claim 15, wherein the immune checkpoint inhibitor is Ipilimumab.

17. An assay kit comprising the monoclonal antibody of claim 1 that specifically recognizes and binds to a peptide having the N-terminus amino acid sequence MGNTGPTGAV (SEQ ID NO. 1), and at least one of: a streptavidin coated well plate; a C-terminal biotinylated peptide having the N-terminus amino acid sequence MGNTGPTGAV (SEQ ID No. 1); a calibrator peptide having the N-terminus amino acid sequence MGNTGPTGAV (SEQ ID NO. 1), an antibody biotinylation kit; an antibody HRP labeling kit; an antibody radiolabeling kit; or an assay visualization kit.

18. The assay kit of claim 17, wherein the monoclonal antibody is a monoclonal antibody raised against a synthetic peptide having the N-terminus amino acid sequence MGNTGPTGAV (SEQ ID NO. 1).

19. The assay kit of claim 17, wherein the monoclonal antibody does not specifically recognise or bind to a peptide having the N-terminus amino acid sequence selected from the group consisting of XMGNTGPTGAV (SEQ ID No. 2), wherein X represents any amino acid, GNTGPTGAV (SEQ ID NO. 3), MGQTGPTGAV (SEQ ID NO. 4), MGNSGPTGAV (SEQ ID NO. 5), and QGNTGPTGAV (SEQ ID NO. 6).

* * * * *